(12) United States Patent
Kao et al.

(10) Patent No.: US 8,415,160 B2
(45) Date of Patent: Apr. 9, 2013

(54) TRANSFECTION WITH MICRO EXPLOSION ENACTED BY COATED DRY ICE PARTICLES

(75) Inventors: Fu-Jen Kao, Taipei (TW); Yung-En Kuo, Taipei (TW)

(73) Assignee: National Yang Ming University, Taipei (TW)

( * ) Notice: Subject to any disclaimer, the term of this patent is extended or adjusted under 35 U.S.C. 154(b) by 282 days.

(21) Appl. No.: 12/957,035

(22) Filed: Nov. 30, 2010

(65) Prior Publication Data
US 2012/0028356 A1 Feb. 2, 2012

(30) Foreign Application Priority Data

Jul. 27, 2010 (TW) ............................... 99124780 A

(51) Int. Cl.
*C12N 15/87* (2006.01)
(52) U.S. Cl.
USPC . 435/459; 435/470; 435/252.33; 435/254.11; 435/325

(58) Field of Classification Search ........................ None
See application file for complete search history.

(56) References Cited

U.S. PATENT DOCUMENTS

2010/0152651 A1* 6/2010 Boyden et al. .................. 604/66

* cited by examiner

*Primary Examiner* — Jim Ketter
(74) *Attorney, Agent, or Firm* — Muncy, Geissler, Olds & Lowe, PLLC

(57) ABSTRACT

Disclosed is a transfection method, which includes the steps of: (a) adhering the gene fragments to dry ice particles; (b) adding the dry ice particles into the medium/liquid that contains target cells; and (c) transporting the gene fragments into the target cells via the micro explosion/sublimation of the dry ice particles. In addition, the gene fragments can also adhere first to nanoparticles, which can then adhere to dry ice particles. Subsequently, gene fragments enter cells by micro explosion/sublimation. The present invention can be applied in transgenic research on prokaryotic, eukaryotic, plant and animal cells and in the development of new species in agriculture.

10 Claims, 6 Drawing Sheets

TRANSFECTION WITH MICRO EXPLOSION ENACTED BY COATED DRY ICE PARTICLES

CROSS-REFERENCED TO RELATED APPLICATIONS

The present invention claims the priority of Taiwan Patent Application No. 099124780 filed Jul. 27, 2010.

FIELD OF THE INVENTION

The present invention relates to a method and system of transfection. Particularly, the present invention relates to a method and system of transfection which uses the micro explosion of dry ice particles to raise the transfection efficiency.

BACKGROUND OF THE INVENTION

Transfection or transplantation technology is used to transport deoxyribonucleic acid (DNA), ribonucleic acid (RNA) and other biological materials into living cells and a tool for gene research and the expression therefor. At present, generic transfection method includes following several types. (1) In "chemical assay", calcium phosphate ($Ca_3(PO_4)_2$) or cationic polymer is usually used. For example, plasmid DNA is transported into a bacterium using $Ca_3(PO_4)_2$ precipitation method with an efficiency of approximately 1%. (2) "Non-chemical assay" includes electroporation, sono-poration, optical transfection, etc. In electroporation, for example, an electric field is temporarily applied to the cells; some opened pores are temporarily generated on the plasma membrane, and plasmic DNA therefore enters the cells. However, the success of electroporation depends on the excellent preparation of cells and plasmid DNA, and this process cannot be applied to all cell types. (3) "Particle transfection assay" includes gene gun, magnetic particle-assisted transfection, impalefection, etc. In a gene gun, for example, metal particles act as carriers and high-pressured gas is added to accelerate and transport the biological materials on the metal particles into cells or tissues. However, it increase the costs of the equipment, such as gas acceleration tube, pressure membrane, stop valve and vacuum chamber, etc. (4) "Virus assay" is performed by incorporating the target gene into the virus gene and then infecting the host with a generic modified virus, such that the target gene expresses abundantly or inhibits the expression of other gene(s). However, the virus carrier has problems such as limited genetic capacity, lack of safety, etc. (5) "Other assays" includes hybridization, heat shock, nucleofection, etc. Nevertheless, the above-mentioned generic transfection assays still have some drawbacks, including a low generic transfection efficiency, the high experimental equipment cost, complicated experimental assays, damage to cells or tissues upon transfection, problems of safety, and others.

In addition, U.S. Pat. No. 6,503,755 discloses a method in which polynucleotide molecules are transported into non-adhering cells, wherein the ligand adheres to the surface of the support and conjugates on the surface with the antigen of the non-adhering cells. The polynucleotide molecules in the liquid then have opportunity to collide with the non-adhering cells by agitation, and are thus transfected into non-adhering cells. However, this method depend on the experimental skill of anchoring the non-adhering cells. When the anchoring is poor, the efficiency of the transfection of the polynucleotide molecules into the cells is low.

In view of the foregoing, there is a need for a method in transfecting cells which is simple and results in high transfection efficiencies. Therefore, the present invention aims to deal with the above situation.

SUMMARY OF THE INVENTION

The transfection of the present invention uses a method similar to the bioballistic technique to achieve the transfection effect by particles. First, the material to be transfected is adhered to the surface or the interior of dry ice particles, which are then sprayed on a medium or solution of cells. Since dry ice undergoes sublimation from a solid phase to a gas phase at normal temperature and pressure (NTP), dry ice particles sublimate immediately upon contact with the medium or solution because they are exposed to heat, and they undergo micro explosions within it. Thus, the material that adheres to the dry ice particles gains kinetic energy and may penetrate through the cellular surface or the surface of tissue to achieve the transfection efficiency. Considering the volume of a sphere is $V=4/3\pi r^3$, and the surface area of a sphere is $A=4\pi r^2$ where r is the radius of the sphere, the area-volume ratio is thus $A/V=3/r$. Similarly the volume of a cube is $V=a^3$, and the surface area of a cube is $A=6a^2$ where "a" is length of each side of the cube, its area-volume ratio of cube is $A/V=6/a$. From these equations, "$A/V=3/r$" and "$A/V=6/a$", smaller sphere or cube has a larger area-volume ratio. When the size of dry ice particle decreases to the micrometer level, it rapidly sublimates and vaporizes after exposure to heat, causing micro explosions. Therefore, the new transfection method of the present invention is less complicated than particle transfection assay using a gene gun, etc. It therefore reduces the cost of experimental assay, and transports more biological material into the cells than the virus assay. It is also safer than the virus assay.

The novel technique in the present invention can be applied in the field of biotechnology, including transfection to prokaryotes, eukaryotes and plant cells, and the development of new species in agriculture. Therefore, bacteria, fungi, plant cells, insect cells and animal cells are chosen as experimental cells, and the tissues formed from cellular aggregation are chosen as the experimental materials. Biomaterial includes but is not limited to DNA, RNA, complementary DNA (cDNA), small interfering RNA (siRNA), protein, peptide chain, virus and mitochondria, etc. The material that sublimates from the solid phase to a gas phase under NTP can be the carrier of biomaterial, including dry ice, ammonium chloride, iodine, naphthalene, anhydrous ferric chloride and anhydrous aluminum chloride, etc.

The above objectives and advantages of the present invention will become more readily apparent to those ordinarily skilled in the art after reviewing the following detailed descriptions and accompanying drawings.

DETAILED DESCRIPTION OF THE PREFERRED EMBODIMENT

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

Figure 1A:
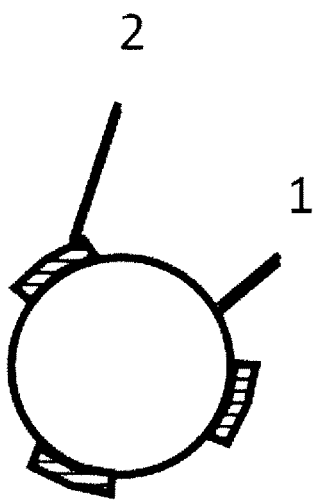
FIGS. 1(a) to 1(c) depict the diagrams of the transfection method in the first preferred embodiment of the present invention.
Figure 1B:
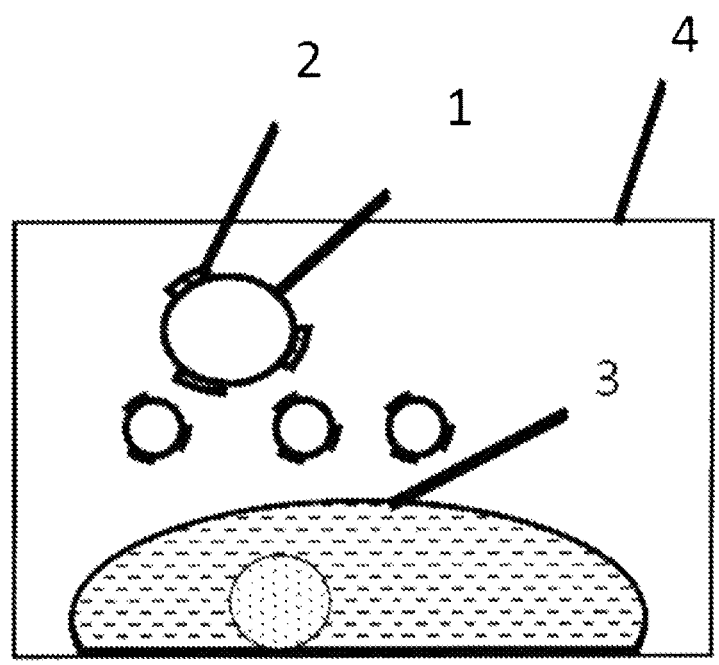
Figure 1C:
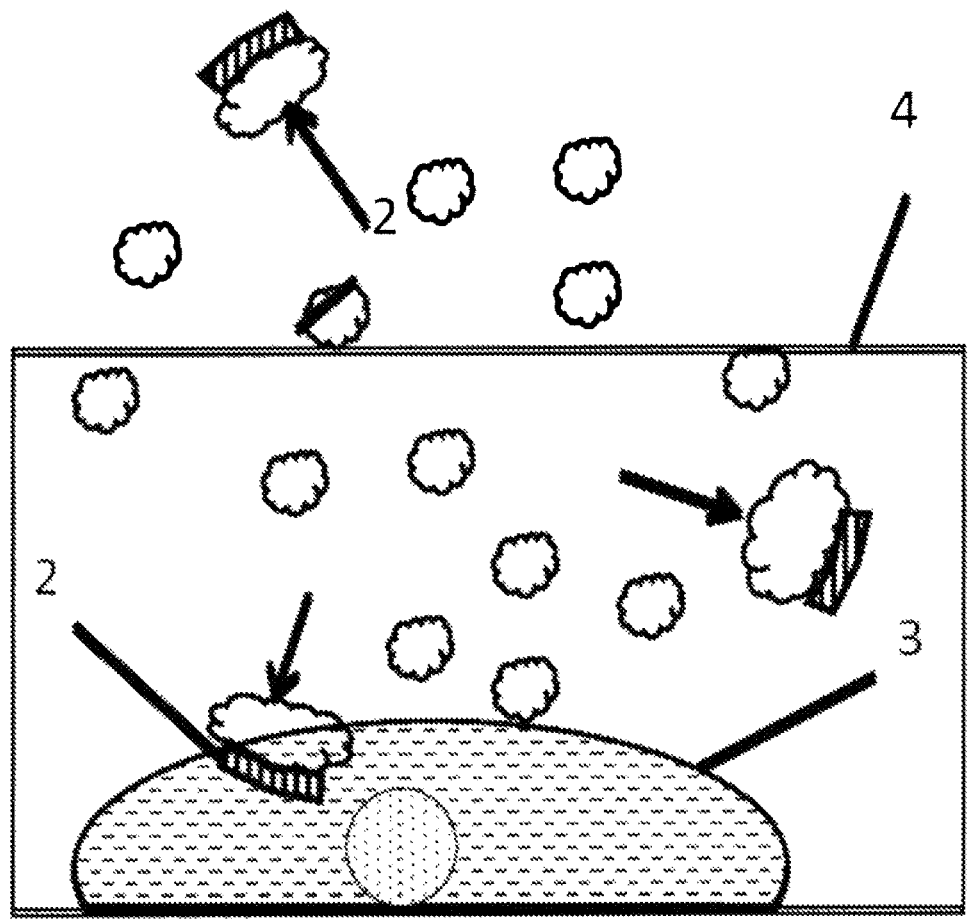

The first preferred embodiment;

Please refer to the transfection method in FIGS. 1(a) to 1(c), first, DNA transfection fragments 2 are adhered to dry ice particle 1, which has a size of one to tens of micrometers. DNA transfection fragment 2 also can be replaced with other biological material such as RNA, cDNA, siRNA, protein, peptide chain, virus and mitochondria, etc. on demand. Not only does DNA transfection fragment 2 adhere to the surface of dry ice particle 1, it also can be mixed into dry ice particle 1. Dry ice particle 1 also can be replaced with other material that sublimates from a solid phase to a gas phase at a normal temperature and pressure (NTP), such as ammonium chloride, iodide, naphthalene, anhydrous ferric chloride and anhydrous aluminum chloride, etc. Next, dry ice particle 1 carrying DNA transfection fragments 2 is directly sprayed onto the medium 4, which contains cells 3. Dry ice particle 1 undergoes a micro explosion owing to sublimation, causing DNA transfection fragment 2 obtains kinetic energy to break through cell membrane to enter cells 3. Not only DNA transfection fragment 2 enter cells 3, dry ice particle 1 may also enter the cells with the DNA transfection fragment 2. However, since dry ice sublimates as carbon dioxide gas, and the concentration of $CO_2$ is relatively low, dry ice does not damage cells. DNA transfection fragment 2 then incorporates into the genome of cells 3 or expresses in the cells 3 by itself.

In this preferred embodiment, the height of medium 4 in the container is approximately cellular thickness, shortening the route along which dry ice particle 1 carries DNA transfection fragment 2 to come into contacts with medium 4 and enters cells 3. Furthermore, medium 4 also can be replaced with another liquid, such as sterile water, a solution that is supplemented with organic ions/inorganic ions or another.

Figure 2A:
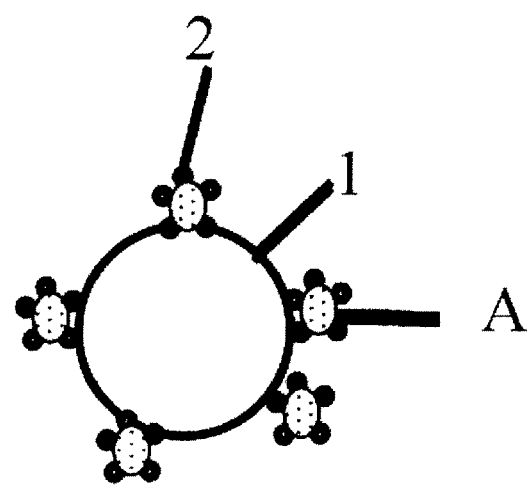
FIGS. 2(a) to 2(c) depict the diagrams of the transfection method in the second preferred embodiment of the present invention.
Figure 2B:
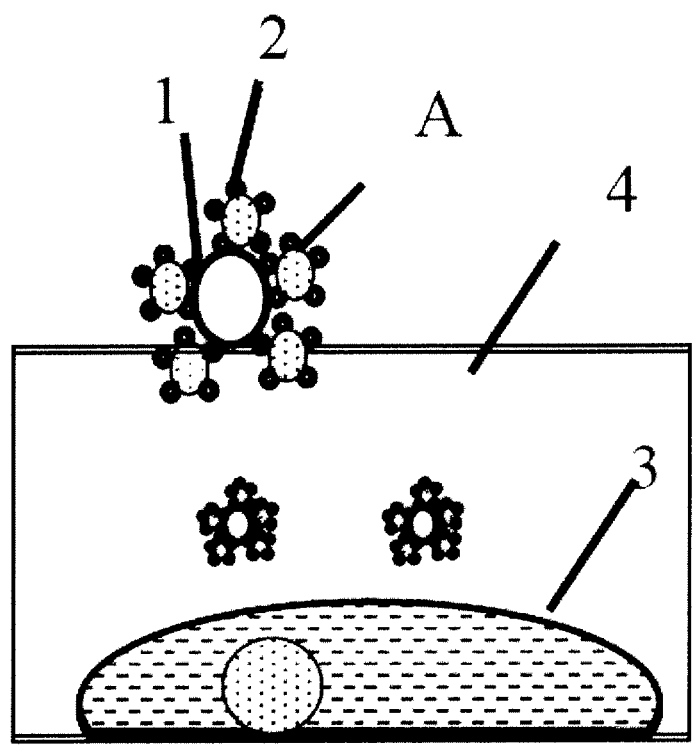
Figure 2C:
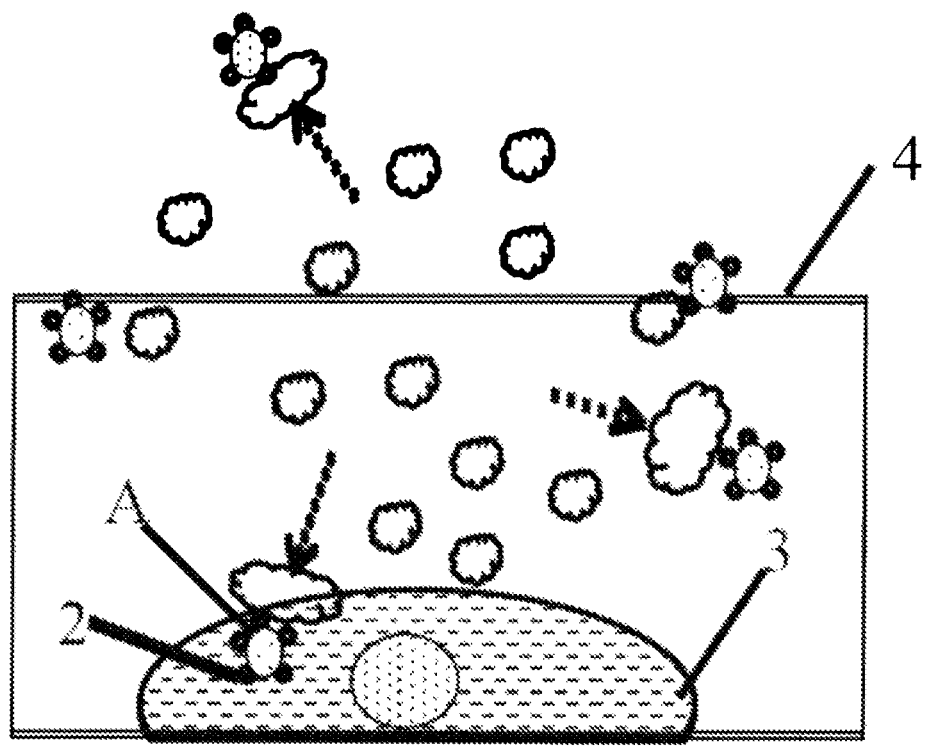

The second preferred embodiment:

Please refer to the transfection method in FIGS. 2(a) to 2(c), first, DNA transfection fragment 2 is adhered to the surface of particle A, which adheres onto dry ice particle 1 with a size of five to tens of micrometers. Particle A also is mixed into dry ice particle 1. It can be a gold nanoparticle, a silver nanoparticle, a diamond nanoparticle or one of many others. Next, dry ice particle 1 carrying particle A, is sprayed directly onto the medium 4, containing cells 3. As described in the first preferred embodiment, the dry ice undergoes a micro explosion by sublimation, and so particle A, carrying DNA transfection fragment 2, obtains sufficient kinetic energy to break through the cell membrane and enter cells 3. Alternatively, only DNA transfection fragment 2 enters the cells. Since particle A has a larger density than DNA transfection fragment 2, particle A can gain more kinetic energy, increasing the probability of DNA transfection fragment 2 enters cells 3.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A transfection method, comprising:
   (a) adhering a gene fragment to a dry ice particle;
   (b) adding the dry ice particle into a liquid that contains cells; and
   (c) transporting the gene fragment into the cells via a micro explosion caused by sublimation of the dry ice.

2. The method according to claim 1, wherein the step (a) further comprises:
   (a1) adhering the gene fragment first to a particle, which can then adhere to the dry ice particle.

3. The method according to claim 1, wherein both the particle and the gene fragment enter the cells, or only the gene fragment enters the cells.

4. A transfection method, comprising:
   (a) adhering a biological material on a first material which can sublimate from a solid phase to a gas phase at normal temperature and pressure;
   (b) adding the first material with adherent biological material to a medium that contains cells; and
   (c) sublimating the first material to make the biological material to enter the cells.

5. The method according to claim 4, wherein the step (a) further comprises:
   (a1) adhering the biological material to a second material at first, and then adhering the second material to the first material.

6. A transfection system, comprising:
   (a) a cell;
   (b) a first material that sublimates from a solid phase to a gas phase at a (b) normal temperature and pressure;
   (c) a biological material adhered to the first material, the biological material is transported into the cells via a sublimation of the first material.

7. The transfection system according to claim 6 further comprising a second material, wherein the biological material adheres to the second material, and the second material with the biological material adheres to the first material.

8. The transfection system according to claim 6, wherein both the second material and the biological material are transported into the cell, or only the biological material is transported therein to.

9. The transfection system according to claim 6, wherein the cell comprises a bacterium, a fungus, a plant cell, an insect cell or an animal cell; the biological material comprises a deoxyribonucleic acid (DNA), a ribonucleic acid (RNA), a complementary DNA (cDNA), a small interfering RNA (siRNA), a protein, a peptide chain, a virus or a mitochondria; the first material comprises a dry ice particle, an ammonium chloride, an iodine, a naphthalene, an anhydrous ferric chloride or an anhydrous aluminum chloride; and the second material comprises a nanoparticle.

10. The transfection system according to claim 9, wherein the nanoparticle comprises a gold nanoparticle, a silver nanoparticle or a diamond nanoparticle.

* * * * *